US012513474B2

(12) United States Patent
Pontoppidan et al.

(10) Patent No.: US 12,513,474 B2
(45) Date of Patent: Dec. 30, 2025

(54) HEARING AID WITH COGNITIVE ADAPTATION AND METHODS THEREOF

(71) Applicant: Oticon A/S, Smørum (DK)

(72) Inventors: Niels Henrik Pontoppidan, Smørum (DK); Dorothea Wendt, Smørum (DK); Hamish Innes-Brown, Smørum (DK)

(73) Assignee: Oticon A/S, Smørum (DK)

( * ) Notice: Subject to any disclaimer, the term of this patent is extended or adjusted under 35 U.S.C. 154(b) by 155 days.

(21) Appl. No.: 18/608,973

(22) Filed: Mar. 19, 2024

(65) Prior Publication Data

US 2024/0348992 A1 Oct. 17, 2024

(30) Foreign Application Priority Data

Apr. 11, 2023 (EP) .................................... 23167319

(51) Int. Cl.
*H04R 25/00* (2006.01)
*A61B 5/024* (2006.01)

(52) U.S. Cl.
CPC ....... *H04R 25/505* (2013.01); *A61B 5/02438* (2013.01); *H04R 2225/41* (2013.01); *H04R 2225/43* (2013.01)

(58) Field of Classification Search
CPC .. H04R 25/505; H04R 25/70; H04R 2225/41; H04R 2225/43; H04R 25/30; H04R 2225/39; A61B 5/123; A61B 5/121
See application file for complete search history.

(56) References Cited

U.S. PATENT DOCUMENTS

2019/0069098 A1* 2/2019 Walsh .................. H04R 25/505
2019/0182606 A1* 6/2019 Petersen ................ A61B 5/291
2022/0272465 A1 8/2022 Boldt

FOREIGN PATENT DOCUMENTS

DE 102020114770 A1 * 12/2021 ............. A61B 5/121
EP 4106350 A1 * 12/2022 ............. H04R 25/70

* cited by examiner

*Primary Examiner* — Kile O Blair

(57) ABSTRACT

Disclosed herein are embodiments of a method of cognitive adaptation which can be used for a hearing aid to a user. The method includes determining effort and environmental sound distributions over time and modifying settings of the hearing aid based on the optimization of estimations of future effort and environment.

15 Claims, 6 Drawing Sheets

HEARING AID WITH COGNITIVE ADAPTATION AND METHODS THEREOF

SUMMARY

A Hearing Aid:

In an aspect of the present application, a method of cognitive adaptation for a hearing aid to a user is provided. The method includes determining, based on environmental data obtained by the hearing aid over a time period, an environmental difficulty distribution over said time period. The method includes determining, based on physiological data of the user over the time period, an effort distribution over said time period. The method can include determining, based on the environmental difficulty distribution and the effort distribution, a setting distribution of the hearing aid indicative of a hearing setting of the hearing aid over said time period configured to optimize the effort distribution. The method can include generating, based on the environmental difficulty distribution and the effort distribution, a plurality of estimated future time periods, each of the plurality of estimated future time periods comprising an estimated environmental difficulty distribution and an estimated effort distribution. The method can include applying the setting distribution to each of the plurality of future time periods for determination of an optimized effort distribution. The method can include determining, based on the optimized effort distribution, an updated setting distribution. The method includes applying the updated setting distribution to the hearing aid.

Embodiments of the disclosed method can be performed by the hearing aid. Embodiments of the disclosed method can be performed by an auxiliary (e.g., secondary) device. The auxiliary device can be, for example, one or more of: a server, a processing unit, a cloud, and a mobile telephone. Embodiments of the disclosed method can be performed by a combination of a hearing aid and one or more secondary devices. The hearing aid may be adapted to provide a frequency dependent gain and/or a level dependent compression and/or a transposition (with or without frequency compression) of one or more frequency ranges to one or more other frequency ranges, e.g. to compensate for a hearing impairment of a user. The hearing aid may comprise a signal processor for enhancing the input signals and providing a processed output signal.

Advantageously, the disclosed methods allow for the determination and application of improved hearing aid settings, which can then improve the hearing aid user's listening experience. For example, the disclosed methods can provide analysis over a period of time for a number of different listening experiences for the user and can provide a personalized setting distribution that can be incorporated into the hearing aid. The methods can utilize backward-looking and forward-looking analysis of hearing aid settings for determining the most beneficial hearing aid settings for a user. Embodiments of the disclosed embodiments of a method can be advantageous to optimize the effort of the hearing aid user to maintain motivation in a listening environment.

Further, fitting and use of hearing aids is based on audiogram and personalization questions which fail to adequately take cognition into account, as well as the dynamic impact of listening-related fatigue. Cognition is important for hearing and hearing aid fitting, as hearing loss generally raises the effort that a person needs to put into understanding speech in noise compared to normal hearing, and because the baseline cognitive capability impacts how much effort it takes. The fatigue state and the dynamics of fatigue further modify these relationships between hearing performance, effort, and cognitive abilities. These dynamic effects are not part of state-of-art hearing aid fitting.

Advantageously, the disclosed methods can estimate a user's cognitive capability and take it into account when adjusting one or more hearing aid settings. This can allow an improved experience to the user, as the hearing aid may provide beneficial effects specific to a user's cognitive profile.

In one or more example methods, the method disclosed method can take advantage of a digital twin for determining hearing aid settings and/or cognitive adaptation.

In one or more example methods, the method can include obtaining environmental data, such as obtaining the environmental data by the hearing aid. The method can include obtaining the environmental data obtained by the hearing aid over a time period. The environmental data can be indicative of the sound and/or noise environment around the hearing aid. For example, the method can include obtaining the environmental data by an input unit of the hearing aid. The input unit can be, for example, one or more microphones. The environmental data can include a conversion of the sound obtained by the hearing aid to electrical signals. In one or more example methods, the the environmental data comprises one or more of: sound pressure level, signal to noise ratio, and noise floor. In other words, the environmental data includes one or more of sound pressure level, signal to noise ratio, and noise floor of the environment around the hearing aid. The environmental data can be in frequency bands and/or in a full bandwidth and/or in weighted frequency bands. The environmental data can be indicative of the listening environment around the hearing aid. The environmental data can be an electronic representation (e.g., an electrical input signal) representing the sounds and/or noises around the hearing aid.

The hearing aid may comprise an input unit for providing an electric input signal representing sound. The input unit may comprise an input transducer, e.g. a microphone, for converting an input sound to an electric input signal. The input unit may comprise a wireless receiver for receiving a wireless signal comprising or representing sound and for providing an electric input signal representing said sound. For example, the input unit can obtain the environmental data. The hearing aid may comprise a directional microphone system adapted to spatially filter sounds from the environment, and thereby enhance a target acoustic source among a multitude of acoustic sources in the local environment of the user wearing the hearing aid. The directional system may be adapted to detect (such as adaptively detect) from which direction a particular part of the microphone signal originates. This can be achieved in various different ways as e.g. described in the prior art. In hearing aids, a microphone array beamformer is often used for spatially attenuating background noise sources. The beamformer may comprise a linear constraint minimum variance (LCMV) beamformer. Many beamformer variants can be found in literature. The minimum variance distortionless response (MVDR) beamformer is widely used in microphone array signal processing. Ideally the MVDR beamformer keeps the signals from the target direction (also referred to as the look direction) unchanged, while attenuating sound signals from other directions maximally. The generalized sidelobe canceller (GSC) structure is an equivalent representation of the MVDR beamformer offering computational and numerical advantages over a direct implementation in its original form.

The hearing aid may comprise a classification unit configured to classify the current situation based on input signals from (at least some of) detectors, input unit, and possibly other inputs as well. The method may be configured to classify the environmental data for determination of the environmental difficulty. In the present context 'a current situation' may be taken to be defined by one or more of:

a) the physical environment (e.g. including the current electromagnetic environment, e.g. the occurrence of electromagnetic signals (e.g. comprising audio and/or control signals) intended or not intended for reception by the hearing aid, or other properties of the current environment than acoustic);
b) the current acoustic situation (input level, feedback, etc.), and
c) the current mode or state of the user (movement, temperature, cognitive load, etc.);
d) the current mode or state of the hearing aid (program selected, time elapsed since last user interaction, etc.) and/or of another device in communication with the hearing aid.

The classification unit may be based on or comprise a neural network, e.g. a trained neural network. The environmental difficulty distribution can be based on the classification.

The method can be applied (e.g., performed, in operation) over a time period. For example, method can include obtaining the environmental data over a time period. The time period can be adjusted as desired. It may be advantageous for the time period to longer in order to obtain more environmental data. For example, longer time period may allow for more accurate results for the eventual updated setting distribution. However, a time period that is shorter can have uses as well, such as for quick changes to the updated setting distribution. The time period can include taking at least two points of environmental data. The time period can include taking a plurality of environmental data.

In one or more example methods, the time period is a week. In one or more example methods, the time period is a week or greater. The time period can be one or more of, an hour, a day, a week, a month, and a year. In certain examples, the method can continue to operate throughout use of the hearing aid, so the time period can continue to increase as more environmental data and/or physiological data is obtained.

Based on the environmental data obtained, the method can include determining an environmental difficulty distribution over said time period (e.g., difficulty distribution, demand distribution). The environmental difficulty distribution can be indicative of the environmental difficulty around the hearing aid. For example, a cocktail party may have a high environmental difficulty due to the number and complexity of sound sources around the hearing aid. If the user is sitting at home and reading, the environmental difficulty may be lower due to the limited sound sources. The method can use the environmental data to determine the particular environmental difficulty. The method can include classifying the environmental data for determination of the environmental difficulty distribution.

The environmental difficulty distribution can be indicative of the difficulty of the hearing around the user over the time period. The environmental difficulty distribution can be indicative of an estimated difficulty of the hearing around the user over the time period. For example, the environmental difficulty distribution may vary throughout the time period as the user interacts with different environmental situations as indicated by the environmental data. The environmental difficulty distribution may be converted into a function for analyzing the specifics of the data of the environmental difficulty distribution. The method can include determining an environmental function representative of the environmental difficulty distribution.

The hearing aid may comprise a voice activity detector (VAD) for estimating whether or not (or with what probability) an input signal comprises a voice signal (at a given point in time). Accordingly, the method can determine whether the environmental data is a voice signal. A voice signal may in the present context be taken to include a speech signal from a human being. It may also include other forms of utterances generated by the human speech system (e.g. singing). The method can include classifying, based on the voice activity detector unit, a current acoustic environment of the user as a VOICE or NO-VOICE environment, which can then be used for determining the environmental difficulty distribution. This has the advantage that time segments of the electric microphone signal comprising human utterances (e.g. speech) in the user's environment can be identified, and thus separated from time segments only (or mainly) comprising other sound sources (e.g. artificially generated noise). The voice activity detector may be adapted to detect as a VOICE also the user's own voice. Alternatively, the voice activity detector may be adapted to exclude a user's own voice from the detection of a VOICE.

The hearing aid may comprise an own voice detector for estimating whether or not (or with what probability) a given input sound (e.g. a voice, e.g. speech) originates from the voice of the user of the system. The method can include obtaining a voice parameter indicative of whether or not the environmental data is indicative of a voice of the user. A microphone system of the hearing aid may be adapted to be able to differentiate between a user's own voice and another person's voice and possibly from NON-voice sounds.

In one or more examples, the method can include determining the environmental difficulty distribution based on obtained data from a voice detector. In one or more examples, determining the environmental difficulty distribution comprises determining, based on environmental data indicative of voice data from the voice detector, the environmental difficulty distribution.

In one or more example methods, the method can include obtaining physiological data of a user over the time period. In one or more example methods, the physiological data can be pulse data. The physiological data can be indicative of a user's pulse data. Pulse data can be indicative of the effort a user is putting into listening to a particular sound environment. In certain examples, pulse data can be used as a correlation of the effort of a user. However, other types of physiological data can be used as well. For example, the physiological data can be indicative of a user's respiration. The physiological data can be indicative of a user's respiration in combination with motion (such as from an accelerometer).

In one or more example methods, the method can include discounting, such as attenuating, an impact of any physical movement of the user on the pulse data. In order to assess the listening effort, and thus discarding physical effort, the method can include correcting for (estimating and subtracting) effort associated with movement.

In one or more example methods, the method includes obtaining the physiological data from the hearing aid. For example, the hearing aid may have one or more sensors to provide the physiological data. In one or more examples, the one or more sensors may be located in the user's ear-canal. For example, the hearing aid can include an inward-facing microphone. The hearing aid could include an optical sensor. For example, the optical sensor may be a photoplethysmography (PPG) sensor and/or a near infrared spectroscopy (NIRS) sensor. The physiological data can be optical data. In one or more example methods, the method includes obtaining the pulse data from an external device. The external device can be, for example, a smart watch. The external data can be a heart rate monitor. The external device can be a pulse oximeter.

The physiological data, for example indictive of effort and/or fatigue (e.g., effort data and/or fatigue data), can be either measured objectively or estimated subjectively from user input. In certain examples, the method can include obtaining user effort data, which can be the physiological data. The method can obtain the physiological data, for example, from heart rate monitor, e.g. stress levels and body battery or daily readiness.

The hearing aid may comprise a number of detectors configured to provide status signals relating to a current physical environment of the hearing aid (e.g. the current acoustic environment, the environmental data), and/or to a current state of the user wearing the hearing aid (e.g., the physiological data, such as pulse data), and/or to a current state or mode of operation of the hearing aid. Alternatively or additionally, one or more detectors may form part of an external device in communication (e.g. wirelessly) with the hearing aid. An external device may e.g. comprise another hearing aid, a remote control, and audio delivery device, a telephone (e.g. a smartphone), an external sensor, etc.

The hearing aid may comprise antenna and transceiver circuitry allowing a wireless link to an external device, such as a smart watch, an entertainment device (e.g. a TV-set), a communication device (e.g. a telephone), a wireless microphone, or another hearing aid, etc. The hearing aid may thus be configured to wirelessly receive a direct electric input signal from another device. Likewise, the hearing aid may be configured to wirelessly transmit a direct electric output signal to another device. The direct electric input or output signal may represent or comprise an audio signal and/or a control signal and/or an information signal. In general, a wireless link established by antenna and transceiver circuitry of the hearing aid can be of any type. The wireless link may be a link based on near-field communication, e.g. an inductive link based on an inductive coupling between antenna coils of transmitter and receiver parts. The wireless link may be based on far-field, electromagnetic radiation. Preferably, frequencies used to establish a communication link between the hearing aid and the other device is below 70 GHz, e.g. located in a range from 50 MHz to 70 GHz, e.g. above 300 MHz, e.g. in an ISM range above 300 MHz, e.g. in the 900 MHz range or in the 2.4 GHz range or in the 5.8 GHz range or in the 60 GHz range (ISM=Industrial, Scientific and Medical, such standardized ranges being e.g. defined by the International Telecommunication Union, ITU). The wireless link may be based on a standardized or proprietary technology. The wireless link may be based on Bluetooth technology (e.g. Bluetooth Low-Energy technology), or Ultra WideBand (UWB) technology.

In one or more examples, the method can include communicating with the external device. For example, the method can include transmitting a request for data from the external device. The method can include obtaining (e.g., receiving) the physiological data from the external device.

The method can be applied (e.g., performed, in operation) over a time period. For example, the method can include obtaining the physiological data over a time period. The time period can be adjusted as desired. It may be advantageous for the time period to longer in order to obtain more physiological data. For example, a longer time period may allow for more accurate results for the eventual updated setting distribution. However, a time period that is shorter can have uses as well, such as for quick changes to the updated setting distribution. The time period can include taking at least two points of physiological data. The time period can include taking a plurality of physiological data.

The method can include determining an effort distribution based on the physiological data over the time period. For example, the effort distribution can be indicative of how much effort a user is applying to listening in the listening environment. In the example using pulse data as physiological data, higher pulse data can be indicative of increased effort in the effort distribution whereas lower pulse data can be indicative of decreased effort in the effort distribution. For example, the effort distribution may vary throughout the time period as the user interacts with different environmental situations. The effort distribution may be converted into a function for analyzing the specifics of the data of the effort distribution. The effort distribution can be used to derive and/or predict the fatigue state of the user.

In some examples, as the method includes determining the environmental difficulty distribution and the effort distribution over the same time period, the method can include correlating and/or mapping the environmental difficulty distribution and the effort distribution. For example, the method can obtain the environmental data and the physiological data at the same times during the time period. For example, the method can obtain the environmental data and the physiological data at the same intervals within the time period. Example intervals are every second, every minute, every five minutes, every 30 minutes, every hour, etc. As the physiological data and the environmental data can be taken in the same time intervals, the method can correlate the two. This can allow for a better understanding on how a user's effort relates to the difficulty of the environment.

Based on the environmental difficulty distribution and the effort distribution, the method can include determining a setting distribution of the hearing aid. The setting distribution can include particular settings of the hearing aid. The setting distribution can include one or more settings (e.g., parameters, levels) of the hearing aid. For example, the setting distribution can include one or more of noise attenuation, loudness, directionality attenuation, and other hearing aid settings. The setting distribution can be configured to optimize the effort distribution over the time period. As an example, the method determines the environmental difficulty distribution and the effort distribution for a time period and determines a particular setting distribution that can optimize the effort distribution over that time period. In one or more example methods, optimizing the effort distribution can be advantageous for reducing fatigue of a user, such as listening fatigue.

The hearing aid may be configured to operate in different modes, e.g. a normal mode and one or more specific modes, e.g. selectable by a user, or automatically selectable. A mode of operation may be optimized to a specific acoustic situation or environment, e.g. a communication mode, such as a telephone mode. A mode of operation may include a low-power mode, where functionality of the hearing aid is reduced (e.g. to save power), e.g. to disable wireless communication, and/or to disable specific features of the hearing aid. In one or more examples, the setting distribution can include operating the hearing aid in one or more different modes. Accordingly, applying the setting distribution and/or the updated setting distribution an include transmitting instructions to the hearing aid to change modes.

Optimizing the effort distribution can vary depending on the desires of the user. Optimizing the effort distribution can include minimizing effort for some scenarios but further to maximize effort when needed, i.e. important situation when efficient communications is needed. For example, optimizing the effort distribution can include minimizing the effort distribution. For example, optimizing the effort distribution can include adjusting the effort distribution to be at and/or near a baseline effort indicative of "standard" effort by a user. In some examples, the setting distribution can be determined to make it "easiest" for the user of the hearing aid to listen in a particular set of environments over a time period. In some example methods, the setting distribution may not be applied to the hearing aid upon determination.

In one or more examples, optimizing the effort distribution can include maximizing a cognitive capability estimate of the user. The cognitive capability estimate may be indicative of the cognitive capacity of a user of the hearing aid. By maximizing the cognitive capacity capability of the user, the user may experience less fatigue and may experience more motivation for a particular hearing environment. The cognitive capability estimate may be indicated by the cognitive capability parameter discussed below.

It may be advantageous to improve on the setting distribution so that it can be more robust for different scenarios that a user may experience. Accordingly, it can be useful to fine tune and/or otherwise improve the setting distribution. The method can include generating a plurality of estimated future time periods. The plurality of estimated future time periods can be, for example, a plurality of predicted future time periods. For example, the method can include generating the plurality of estimated future time periods based on the environmental difficulty distribution and the effort distribution. Each of the plurality of estimated future time periods can include an estimated environmental difficulty distribution and an estimated effort distribution. The estimated environmental difficulty distribution and/or estimated effort distribution may be different iterations of values for a difficulty distribution and/or an effort distribution. The estimated environmental difficulty distribution and/or estimated effort distribution may be estimations of what a user will experience during the day. The estimated environmental difficulty distribution and/or estimated effort distribution can be based on previous and/or historical data, such as the environmental difficulty distribution and/or the effort distribution. The estimated environmental difficulty distribution and/or estimated effort distribution can be determined and may not relate to any previous data. Generating the estimated future time periods may include generating a digital twin of the hearing aid.

In one or more example methods, the plurality of estimated future time periods, including the estimated environmental difficulty distribution and the estimated effort distribution, can be simulations of different potential time periods that the user of the hearing aid may encounter. In one or more examples, the generating the plurality of estimated future time periods can include generating a digital twin of the hearing aid. In one or more example methods, the estimated environmental difficulty distribution and/or the estimated effort distribution vary between each of the plurality of future time periods. For example, the method estimates many different future time periods for different listening scenarios that a user of the hearing aid may experience. Further discussion can be found at the articles "Fully Synthetic Longitudinal Real-World Data From Hearing Aid Wears for Public Health Policy Modeling" by Jeppe H. Christensen, et al. (DATA REPORT article, Front. Neurosci., 13 Aug. 2019, Sec. Auditory Cognitive Neuroscience, Volume 13-2019) and "DataSynthesizer: Privacy-Preserving Synthetic Datasets" by Haoyue Ping, et al., (SSDBM '17: Proceedings of the 29th International Conference on Scientific and Statistical Database Management, June 2017, Article No.: 42). Both articles are hereby incorporated by reference in their entirety.

The plurality of estimated future time periods can be the same as the time period. The plurality of estimated future time periods can be different from the time period. For example, the plurality of estimated future time periods may be longer than the time period.

In some examples, upon generation of the plurality of estimated future time periods, the method includes applying the setting distribution to each of the plurality of estimated time periods. Accordingly, the method will apply the setting distribution to a number of estimated time periods in order to obtain data on how the effort distribution will be affected by the setting distribution. As the setting distribution may not be particular useful for certain ones of the plurality of estimated future time periods, the method can determine an optimized effort distribution. What the optimized effort distribution is can vary depending on the desires of the user. In this way, the method does not just use the obtained environmental data and the obtained physiological data for determining a particular setting distribution, but advantageous estimates the setting distribution over a number of different estimated future time periods. This can lead to a more advantageous effort distribution as indicated by the optimized effort distribution. In certain examples, the optimized effort distribution may be the same as the effort distribution. In certain examples, the optimized effort distribution may be different than the effort distribution.

Based on the optimized effort distribution, the method may determine an updated setting distribution. The updated setting distribution may be indicative of the optimized effort distribution. For example, the updated setting distribution may be advantageous for optimizing future effort distributions.

As an example, determining the updated setting distribution can be done by first estimating (e.g., by the generating the plurality of estimated future tie periods) if it is possible for the hearing aid to change the difficulty level (e.g., the effort distribution) in particular situation (this depends on the estimate of difficulty) and the current setting distribution.

For simplicity the optimized effort distribution can be indicative of the SNR and the settings reduced to an input/output SNR difference (deltaSNR). Input SNR is the signal-to-noise ratio at the microphone input of the hearing aid whereas the output SNR is signal-to-noise ratio at the receiver end of the hearing aid (the sound the user listens to), which can be indicated by the environmental data. Depending on the configuration of the hearing aid (e.g., depending on the setting distribution), the sound environment (e.g., as indicated by the environmental data and/or the environmental difficulty distribution) can be so difficult that the hearing aid cannot provide more help (a larger deltaSNR) or it can be so simple, where the noise is so weak that it cannot be attenuated. Accordingly, the method can include determining the updated setting distribution in order to attenuate these values if possible.

The method can the include applying the updated setting distribution to the hearing aid. In this way, in certain examples, the user of the hearing aid will experience a more optimized effort in their listening environment. In certain example methods, the updated setting distribution may be a baseline use of the hearing aid, the setting distribution may be updated by, for example, the user and/or the hearing aid. As used herein, applying the updated setting distribution to the hearing aid can include modifying one or more settings and/or parameter of the hearing aid. As used herein, applying the updated setting distribution to the hearing aid can include transmitting the updated setting distribution to the hearing aid, wherein the updated setting distribution includes instructions on modifying one or more settings and/or parameter of the hearing aid.

The hearing aid may comprise an output unit for providing a stimulus perceived by the user as an acoustic signal based on a processed electric signal. The output unit may comprise a number of electrodes of a cochlear implant (for a CI type hearing aid) or a vibrator of a bone conducting hearing aid. The output unit may comprise an output transducer. The output transducer may comprise a receiver (loudspeaker) for providing the stimulus as an acoustic signal to the user (e.g. in an acoustic (air conduction based) hearing aid). The output transducer may comprise a vibrator for providing the stimulus as mechanical vibration of a skull bone to the user (e.g. in a bone-attached or bone-anchored hearing aid). The output unit may (additionally or alternatively) comprise a transmitter for transmitting sound picked up-by the hearing aid to another device, e.g. a far-end communication partner (e.g. via a network, e.g. in a telephone mode of operation, or in a headset configuration). Applying the updated setting distribution can comprise modifying one or more parameters and/or settings of the output unit.

The hearing aid may comprise a 'forward' (or 'signal') path for processing an audio signal between an input and an output of the hearing aid. A signal processor may be located in the forward path. The signal processor may be adapted to provide a frequency dependent gain according to a user's particular needs (e.g. hearing impairment). The hearing aid may comprise an 'analysis' path comprising functional components for analyzing signals and/or controlling processing of the forward path. Some or all signal processing of the analysis path and/or the forward path may be conducted in the frequency domain, in which case the hearing aid comprises appropriate analysis and synthesis filter banks. Some or all signal processing of the analysis path and/or the forward path may be conducted in the time domain. Applying the updated setting distribution can comprise modifying the forward path.

The hearing aid may comprise an acoustic (and/or mechanical) feedback control (e.g. suppression) or echo-cancelling system. Adaptive feedback cancellation has the ability to track feedback path changes over time. It is typically based on a linear time invariant filter to estimate the feedback path, but its filter weights are updated over time. The filter update may be calculated using stochastic gradient algorithms, including some form of the Least Mean Square (LMS) or the Normalized LMS (NLMS) algorithms. They both have the property to minimize the error signal in the mean square sense with the NLMS additionally normalizing the filter update with respect to the squared Euclidean norm of some reference signal. Applying the updated setting distribution can comprise modifying the acoustic feedback control and/or echo-cancelling system.

In one or more example methods, determining the setting distribution comprises obtaining user input during the time period. In one or more example methods, determining the setting distribution comprises determining, based on the user input, the environmental difficulty distribution and the effort distribution, the setting distribution. In other words, the setting distribution may take into account user input in determining the setting distribution. For example, the user may adjust certain settings and/or parameters of the hearing aid during the time period. The method can include obtaining these user inputs indicative of adjustments of certain settings and/or parameters and combining them with the environmental difficulty distribution and the effort distribution. This may allow for a more accurate, or at least individually user-targeted, setting distribution. However, it may not be necessary to obtain the user input in certain situations and/or examples.

Advantageously, embodiments of the disclose method can be used to determine user motivation (e.g., user engagement). Motivation can be indicative of how interested a user is in a particular environment. In certain examples, the method can include determining, based on the environmental difficulty distribution and the effort distribution, a motivation distribution over said time period. The motivation distribution can be indicative of the motivation of the user over the time period. In certain situations, it may be difficult to determine the motivation distribution based on just the environmental difficulty distribution and the effort distribution. In one or more example methods, the method includes determining, based on the environmental difficulty distribution, the effort distribution, and user motivation input, a motivation distribution over said time period. For example, the method can include obtaining the user motivation input. The user motivation input may be subjective data regarding the user's motivation in a particular time state during the time period. For example, the user motivation input may be indicative of high engagement or low engagement. The user motivation input may be indicative of the user giving up. The method can include determining a particular user motivation parameter based on the user motivation input. For example, the user motivation parameter may be a numerical value and/or numerical function determined based on the user motivation input. In certain examples, the motivation parameter may be a numerical value from 0 to 100, wherein 100 relates to the highest user motivation as indicated by the user motivation input and 0 relates to the lowest user motivation as indicative by the user motivation input.

In one or more examples, determining the motivation distribution can include estimating the listening effort minus the minimal listening effort associated with this complexity and current fatigue level. Examples of determining the motivation distribution can be found in the article "Neural and computational mechanisms of momentary fatigue and persistence in effort-based choice" by Tanja Müller, et al. (Nature Communications, Article number: 4593 (2021)). The article is hereby incorporated by reference in its entirety.

In one or more example methods, generating the plurality of estimated future time periods is based on the motivation distribution, the environmental difficulty distribution, and the effort distribution, the plurality of estimated future time periods, each of the plurality of estimated future time periods comprising an estimated motivation distribution, the estimated environmental difficulty distribution, the estimated effort distribution. In other words, the method can take into account the motivation distribution when generating the plurality of estimated future time periods. Further, the method generates each of the plurality of estimated future time periods also having an estimated motivation distribution. Data synthesis can be used to generate the plurality of estimated future time periods that this user could experience.

In one or more example methods, the method can include determining a cognitive capability parameter. The cognitive capability parameter can be indicative of a dynamic cognitive capability of the user. In one or more example methods, the method can include determining a cognitive capability parameter based on the motivation distribution, the environmental difficulty distribution, and the effort distribution. The cognitive capability parameter may be an estimation of the cognitive capability of the user (for example, the cognitive capability estimate). The cognitive capability parameter may be a cognitive capability distribution over the time period. In one or more example methods, the method can include determining a cognitive capability distribution. The cognitive capability distribution can include a plurality of cognitive capability parameters over the time period. The cognitive capability parameter can be indicative of an early marker for a mental disease. The cognitive capability parameter may be indicative of the cognitive capability estimate. The cognitive capability parameter may be the cognitive capability estimate.

In one or more example methods, the method can determine the cognitive capability parameter by inputting the motivation distribution and/or the environmental difficulty distribution and/or the effort distribution into a model. The method can include receiving an output of the model, the output being indicative of the cognitive capability of the user. In one or more examples, the method integrates the effort over time and further includes individual parameters and/or individual fatigue states of the user.

In one or more example methods, the method can include determining, based on the cognitive capacity parameter, a cognitive capability distribution. The cognitive capability distribution can be indicative of a dynamic cognitive capability of the user over a period of time. For example, the cognitive capability distribution may vary throughout the time period as the user interacts with different environmental situations (such as indicated by the environmental difficulty distribution) with a particular effort (such as indicated by the effort distribution). The cognitive capability distribution may be converted into a function for analyzing the specifics of the data of the cognitive capability distribution. The method can include determining a cognitive capability function representative of the cognitive capability distribution.

In one or more example methods, determining the updated setting distribution is based on the optimized effort distribution and the cognitive capability parameter. In one or more example methods, determining the updated setting distribution is based on the optimized effort distribution and the cognitive capability distribution. In other words, the method can take the cognitive capability parameter and/or distribution into account when determining the updated setting distribution. For example, the updated setting distribution can take into account the cognitive capability parameter in order to achieve optimized setting distributions.

Advantageously, embodiments of the disclosed method can be used iteratively, such as to continuously improve the setting distribution(s) of the hearing aid. As more data is brought into the method, the method can keep improving the user's experience with the hearing aid via setting distribution(s).

In one or more example methods, the method includes generating, based on the estimated environmental difficulty distribution and the estimated effort distribution, a second plurality of estimated future time periods, each of the second plurality of estimated future time periods comprising a second estimated environmental difficulty distribution and a second estimated effort distribution. In one or more example methods, the method includes applying the updated setting distribution to each of the second plurality of future time periods for determination of a second optimized effort distribution. In one or more example methods, the method includes determining, based on the second optimized effort distribution, a second updated setting distribution. In one or more example methods, the method includes applying the second updated setting distribution to the hearing aid. In other words, the method can include repeatedly generating estimated future time periods (e.g., a second plurality of estimated future time periods, a third plurality of future time periods). Each of the plurality of estimated future time period can have respective estimated environmental difficulty distribution(s) and estimated effort distribution(s). The above discussions can be applied to the second plurality of estimated time periods, third plurality of estimated time periods, etc.

In one or more example methods, the environmental data and the physiological data are past data. In one or more example methods, the environmental data and/or the physiological data are past data. In one or more example methods, the environmental data and the physiological data are historical data. For example, the environmental data and/or the physiological data can be stored in a memory, such as a database.

In one or more example methods, the environmental data and the physiological data are live data. In one or more example methods, the environmental data and/or the physiological data are live data. For example, the environmental data and/or the physiological data can be real-time data.

In one or more example methods, the method can include providing the environmental difficulty distribution and the effort distribution to a machine learning model. In one or more example methods, and the setting distribution is output by the machine learning model. In one or more example methods, the method includes obtaining, from an output of the machine learning model, the setting distribution. The same or different machine learning model can be used for obtaining the updated setting distribution.

As used herein, a distribution (for example the environmental difficulty distribution, effort distribution, setting distribution) can be a statistical distribution as a function of time.

In an aspect of the present application, a method of cognitive adaptation for a hearing aid to a user is provided. The method includes determining, based on environmental data obtained by the hearing aid over a time period, an environmental difficulty distribution over said time period. The method includes determining, based on physiological data of the user over the time period, an effort distribution over said time period. The method can include determining, based on the environmental difficulty distribution and the effort distribution, a setting distribution of the hearing aid indicative of a hearing setting of the hearing aid over said time period configured to optimize the effort distribution. The method can include generating, based on the environmental difficulty distribution and the effort distribution, a plurality of estimated future time periods, each of the plurality of estimated future time periods comprising an estimated environmental difficulty distribution and an estimated effort distribution. The method can include applying the setting distribution to each of the plurality of future time periods for determination of a maximized cognitive capability estimate and/or a maximized cognitive capability parameter. The method can include determining, based on the maximized cognitive capability estimate and/or the maximized cognitive capability parameter, an updated setting distribution. The method includes applying the updated setting distribution to the hearing aid.

The hearing aid may further comprise other relevant functionality for the application in question, e.g. compression, noise reduction, etc.

The hearing aid may comprise a hearing instrument, e.g. a hearing instrument adapted for being located at the ear or fully or partially in the ear canal of a user, e.g. a headset, an earphone, an ear protection device or a combination thereof. A hearing system may comprise a speakerphone (comprising a number of input transducers and a number of output transducers, e.g. for use in an audio conference situation), e.g. comprising a beamformer filtering unit, e.g. providing multiple beamforming capabilities.

A Hearing Aid:

In an aspect, a hearing aid configured for cognitive adaptation is disclosed. The hearing aid comprises a memory. The hearing aid comprises interface circuitry. The hearing aid comprises a processor. The processor can be configured to determine, based on environmental data obtained by the hearing aid over a time period, an environmental difficulty distribution over said time period. The processor can be configured to determine, based on physiological data of the user over the time period, an effort distribution over said time period. The processor can be configured to determine, based on the environmental difficulty distribution and the effort distribution, a setting distribution of the hearing aid indicative of a hearing setting of the hearing aid over said time period configured to optimize the effort distribution. The processor can be configured to generate, based on the environmental difficulty distribution and the effort distribution, a plurality of estimated future time periods, each of the plurality of estimated future time periods comprising an estimated environmental difficulty distribution and an estimated effort distribution. The processor can be configured to apply the setting distribution to each of the plurality of future time periods for determination of an optimized effort distribution. The processor can be configured to determine, based on the optimized effort distribution, an updated setting distribution. The hearing aid can be configured to apply the updated setting distribution.

It is intended that some or all of the method features described above, in the 'detailed description of embodiments' or in the claims can be combined with embodiments of the hearing aid, when appropriately substituted by a corresponding process and vice versa. Embodiments of the hearing aid have the same advantages as the corresponding methods. Accordingly, the hearing aid can be configured to perform part and/or all of the methods discussed herein.

A Computer Readable Medium or Data Carrier:

In an aspect, a tangible computer-readable medium (a data carrier) storing a computer program comprising program code means (instructions) for causing a data processing system (a computer) to perform (carry out) at least some (such as a majority or all) of the (steps of the) method described above, in the 'detailed description of embodiments' and in the claims, when said computer program is executed on the data processing system is furthermore provided by the present application.

By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Other storage media include storage in DNA (e.g. in synthesized DNA strands). Combinations of the above should also be included within the scope of computer-readable media. In addition to being stored on a tangible medium, the computer program can also be transmitted via a transmission medium such as a wired or wireless link or a network, e.g. the Internet, and loaded into a data processing system for being executed at a location different from that of the tangible medium.

A Computer Program:

A computer program (product) comprising instructions which, when the program is executed by a computer, cause the computer to carry out (steps of) the method described above, in the detailed description of embodiments' and in the claims is furthermore provided by the present application.

A Data Processing System:

In an aspect, a data processing system comprising a processor and program code means for causing the processor to perform at least some (such as a majority or all) of the steps of the method described above, in the 'detailed description of embodiments' and in the claims is furthermore provided by the present application.

A Hearing System:

In a further aspect, a hearing system comprising a hearing aid as described above, in the 'detailed description of embodiments', and in the claims, AND an external device (e.g., auxiliary device) is moreover provided.

The hearing system may be adapted to establish a communication link between the hearing aid and the external device to provide that information (e.g. control and status signals, possibly audio signals) can be exchanged or forwarded from one to the other.

The external device may comprise a remote control, a smartphone, or other portable or wearable electronic device, such as a smartwatch or the like.

The external device may be constituted by or comprise a remote control for controlling functionality and operation of the hearing aid(s). The function of a remote control may be implemented in a smartphone, the smartphone possibly running an APP allowing to control the functionality of the audio processing device via the smartphone (the hearing aid(s) comprising an appropriate wireless interface to the smartphone, e.g. based on Bluetooth or some other standardized or proprietary scheme).

The external device may be constituted by or comprise an audio gateway device adapted for receiving a multitude of audio signals (e.g. from an entertainment device, e.g. a TV or a music player, a telephone apparatus, e.g. a mobile telephone or a computer, e.g. a PC) and adapted for selecting and/or combining an appropriate one of the received audio signals (or combination of signals) for transmission to the hearing aid.

The external device may be constituted by or comprise another hearing aid. The hearing system may comprise two hearing aids adapted to implement a binaural hearing system, e.g. a binaural hearing aid system.

In one or more examples, the auxiliary device can be a server and/or other processing device separate from the hearing aid. The auxiliary device can be configured to operate the disclosed steps that are more power intensive.

It is intended that some or all of the method features described above, in the 'detailed description of embodiments' or in the claims can be combined with embodiments of the auxiliary device, when appropriately substituted by a corresponding process and vice versa. Embodiments of the auxiliary device have the same advantages as the corresponding methods. Accordingly, the auxiliary device (such as a server and/or processing unit) can be configured to perform part and/or all of the methods discussed herein.

Definitions

In the present context, a hearing aid, e.g. a hearing instrument, refers to a device, which is adapted to improve, augment and/or protect the hearing capability of a user by receiving acoustic signals from the user's surroundings, generating corresponding audio signals, possibly modifying the audio signals and providing the possibly modified audio signals as audible signals to at least one of the user's ears. Such audible signals may e.g. be provided in the form of acoustic signals radiated into the user's outer ears, acoustic signals transferred as mechanical vibrations to the user's inner ears through the bone structure of the user's head and/or through parts of the middle ear as well as electric signals transferred directly or indirectly to the cochlear nerve of the user.

The hearing aid may be configured to be worn in any known way, e.g. as a unit arranged behind the ear with a tube leading radiated acoustic signals into the ear canal or with an output transducer, e.g. a loudspeaker, arranged close to or in the ear canal, as a unit entirely or partly arranged in the pinna and/or in the ear canal, as a unit, e.g. a vibrator, attached to a fixture implanted into the skull bone, as an attachable, or entirely or partly implanted, unit, etc. The hearing aid may comprise a single unit or several units communicating (e.g. acoustically, electrically or optically) with each other. The loudspeaker may be arranged in a housing together with other components of the hearing aid or may be an external unit in itself (possibly in combination with a flexible guiding element, e.g. a dome-like element).

A hearing aid may be adapted to a particular user's needs, e.g. a hearing impairment. A configurable signal processing circuit of the hearing aid may be adapted to apply a frequency and level dependent compressive amplification of an input signal. A customized frequency and level dependent gain (amplification or compression) may be determined in a fitting process by a fitting system based on a user's hearing data, e.g. an audiogram, using a fitting rationale (e.g. adapted to speech). The frequency and level dependent gain may e.g. be embodied in processing parameters, e.g. uploaded to the hearing aid via an interface to a programming device (fitting system) and used by a processing algorithm executed by the configurable signal processing circuit of the hearing aid.

A 'hearing system' refers to a system comprising one or two hearing aids, and a 'binaural hearing system' refers to a system comprising two hearing aids and being adapted to cooperatively provide audible signals to both of the user's ears. Hearing systems or binaural hearing systems may further comprise one or more 'auxiliary devices', which communicate with the hearing aid(s) and affect and/or benefit from the function of the hearing aid(s). Such auxiliary devices may include at least one of a remote control, a remote microphone, an audio gateway device, an entertainment device, e.g. a music player, a wireless communication device, e.g. a mobile phone (such as a smartphone) or a tablet or another device, e.g. comprising a graphical interface. Hearing aids, hearing systems or binaural hearing systems may e.g. be used for compensating for a hearing-impaired person's loss of hearing capability, augmenting or protecting a normal-hearing person's hearing capability and/or conveying electronic audio signals to a person. Hearing aids or hearing systems may e.g. form part of or interact with public-address systems, active ear protection systems, handsfree telephone systems, car audio systems, entertainment (e.g. TV, music playing or karaoke) systems, teleconferencing systems, classroom amplification systems, etc.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

The figures are schematic and simplified for clarity, and they just show details which are essential to the understanding of the disclosure, while other details are left out. Throughout, the same reference signs are used for identical or corresponding parts.

Further scope of applicability of the present disclosure will become apparent from the detailed description given hereinafter. However, it should be understood that the detailed description and specific examples, while indicating preferred embodiments of the disclosure, are given by way of illustration only. Other embodiments may become apparent to those skilled in the art from the following detailed description.

DETAILED DESCRIPTION OF EMBODIMENTS

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include micro-electronic-mechanical systems (MEMS), integrated circuits (e.g. application specific), microprocessors, microcontrollers, digital signal processors (DSPs), field programmable gate arrays (FPGAs), programmable logic devices (PLDs), gated logic, discrete hardware circuits, printed circuit boards (PCB) (e.g. flexible PCBs), and other suitable hardware configured to perform the various functionality described throughout this disclosure, e.g. sensors, e.g. for sensing and/or registering physical properties of the environment, the device, the user, etc. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

The present application relates to the field of hearing aids and methods of use.

Figure 1:
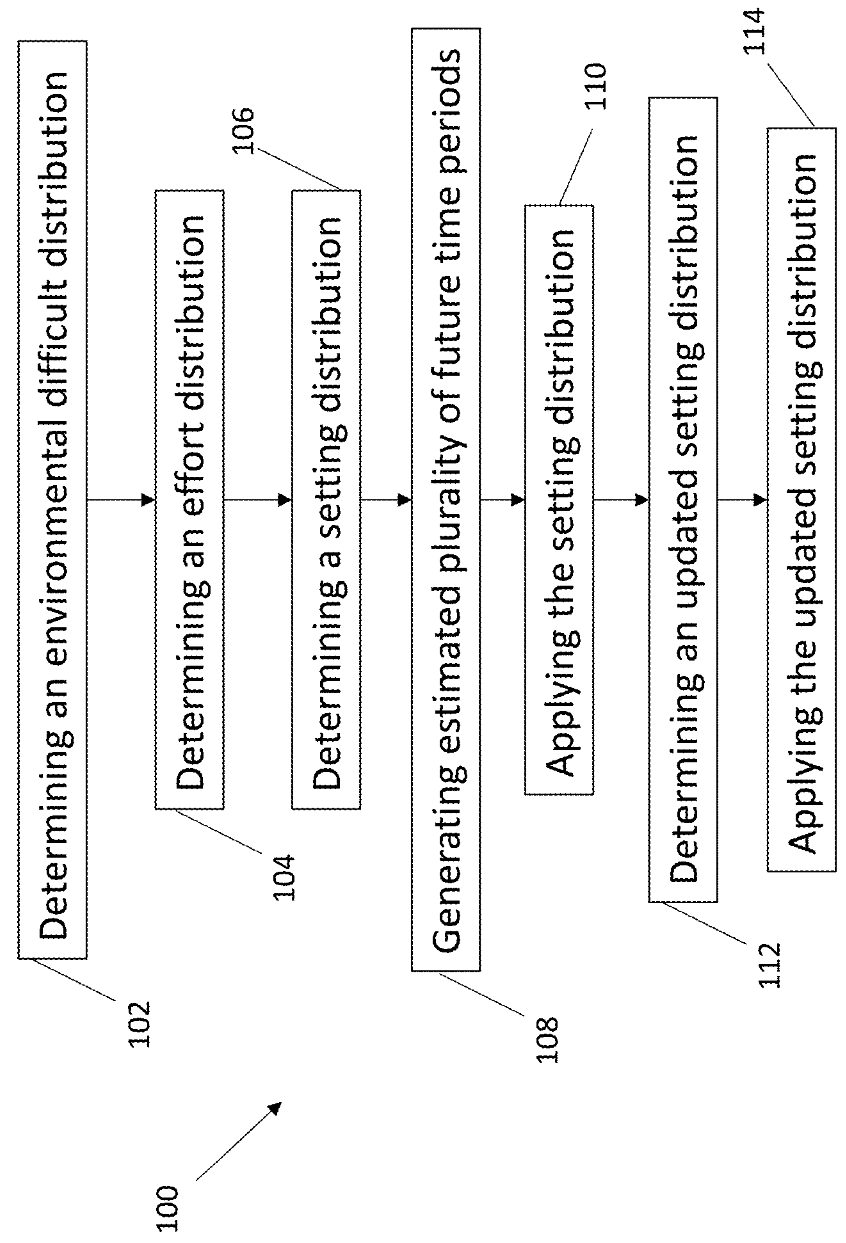
FIG. 1 shows an example method according to the disclosure.

FIG. 1 shows an example method according to the disclosure. The method 100 is for cognitive adaptation for a hearing aid to a user. The method 100 can include determining 102, based on environmental data obtained by the hearing aid over a time period, an environmental difficulty distribution over said time period. The method 100 can include determining 104, based on physiological data of the user over the time period, an effort distribution over said time period. The method 100 can include determining 106, based on the environmental difficulty distribution and the effort distribution, a setting distribution of the hearing aid indicative of a hearing setting of the hearing aid over said time period configured to optimize the effort distribution. The method 100 can include generating 108, based on the environmental difficulty distribution and the effort distribution, a plurality of estimated future time periods, each of the plurality of estimated future time periods comprising an estimated environmental difficulty distribution and an estimated effort distribution. The method 100 can include applying 110 the setting distribution to each of the plurality of estimated future time periods for determination of an optimized effort distribution. The method 100 can include determining 112, based on the optimized effort distribution, an updated setting distribution. The method 100 can include applying 114 the updated setting distribution to the hearing aid. The estimated environmental difficulty distribution and/or the estimated effort distribution can vary between each of the plurality of future time periods. The environmental data can include one or more of: sound pressure level, signal to noise ratio, and noise floor.

Determining 106 the setting distribution can include obtaining user input during the time period, and determining, based on the user input, the environmental difficulty distribution and the effort distribution, the setting distribution.

The method 100 can further include determining, based on the environmental difficulty distribution, the effort distribution, and user motivation input, a motivation distribution over said time period. Generating the estimated plurality of future time periods can be based on the motivation distribution, the environmental difficulty distribution, and the effort distribution, the estimated plurality of future time periods, and each of the estimated plurality of future time periods can include an estimated motivation distribution, the estimated environmental difficulty distribution, the estimated effort distribution.

The method 100 can further include determining a cognitive capability parameter indicative of a dynamic cognitive capability of the user based on the motivation distribution, the environmental difficulty distribution, and the effort distribution. Determining the updated setting distribution can be based on the optimized effort distribution and the cognitive capability parameter.

The method 100 can further include generating, based on the estimated environmental difficulty distribution and the estimated effort distribution, a second estimated plurality of future time periods, each of the second estimated plurality of future time periods comprising a second estimated environmental difficulty distribution and a second estimated effort distribution, applying the updated setting distribution to each of the second plurality of future time periods for determination of a second optimized effort distribution, determining, based on the second optimized effort distribution, a second updated setting distribution, and applying the second updated setting distribution to the hearing aid.

For method 100, the time period can be a week or greater. Other time periods can be used as well. The physiological data can be pulse data. The method 100 can further include obtaining the pulse data from an external device. The environment data and the physiological data can be past data and/or live data. The method 100 can further include providing the environmental difficulty distribution and the effort distribution to a machine learning model and wherein the setting distribution is output by the machine learning model.

Figure 2:
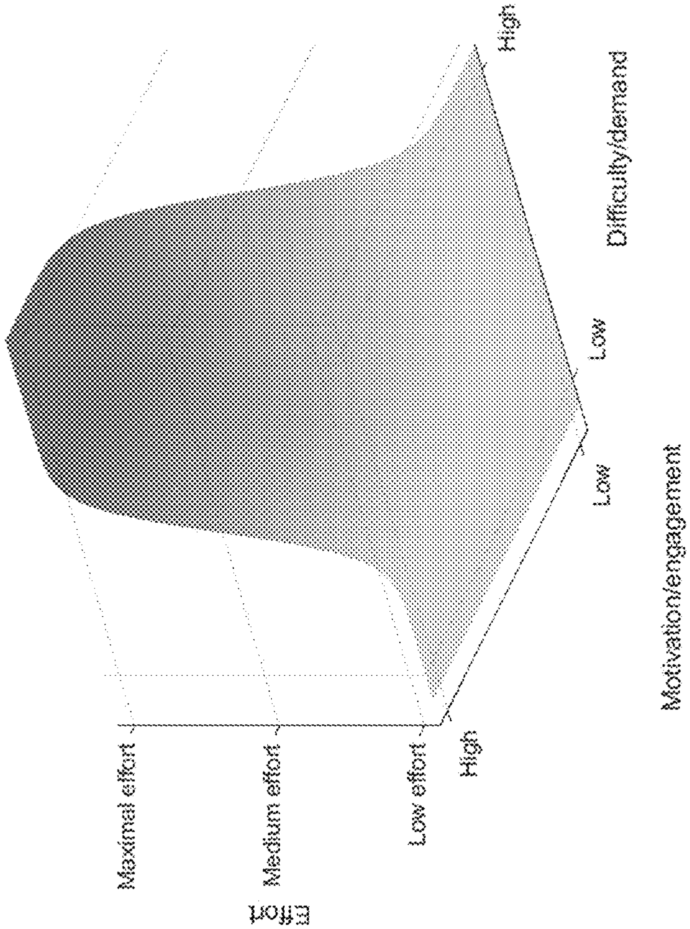
FIG. 2 shows a general example model comparing effort, difficulty, and motivation according to the disclosure.

FIG. 2 shows a general example model comparing effort, difficulty, and motivation according to the disclosure. The model of FIG. 2 can also be known as a FUEL model and/or a dynamic FUEL model. The model describes the effort that a user puts into a certain situation for hearing is a combination of how difficult the situation is and how motivated the person is in engaging in the situation; and high effort is exhibited when both motivation and demand is high. The parametrization of the model is individual so that there is an individual threshold for when it begins to become so difficult that effort goes up, and slope as well as a difficulty where effort cannot be sustained for long, so that motivation drops (aka giving up) which also reduces the effort. Further discussion on the model of FIG. 2 can be found in the article "Hearing Impairment and Cognitive Energy: The Framework for Understanding Effortful Listening (FUEL)" by M. Kathleen Pichora-Fuller, et al., (Ear and Hearing 37 Suppl 1(1): 5S-27S, July 2016). The article is hereby incorporated by reference in its entirety.

Assume a day is started the Fatigue level $F_0$:

$$F(t_0)=F_0,$$

and experience a day with general effort $E_G(t)=E_L(t)+E_R(t)$ as the sum of listening effort and remaining effort:

$$F(t) = \int_{t_0}^{t} g(E_L(t) + E_R(t))\,dt + h(F(t - t'))$$

$$E_L(t) = FUEL\,(SPL(t), SNR(t), F(t), M(t))$$

$$E_{HA+L}(t) = FUEL\,(HA(SPL(t), SNR(t), P(t)), F(t), M(t))$$

Function $g(E_L(t)+E_R(t))$ accounts for that some effort is recoverable right after and that some effort is not recoverable right after (e.g. requires sleep or rest), e.g. depending on whether it exceeds an internal threshold of effort, function h( ) accounts for the decay of fatigue over time, which in it's simplest form could be modelled as an autoregressive process.

The function $E_L(t)$=FUEL(SPL(t), SNR(t), F(t), M(t)) is the dynamic FUEL model (Pichora-Fuller et al 2016) where effort (e.g., effort distribution) is a function of demand/difficulty modelled by SPL(t) and SNR(t), the motivation/engagement (e.g., motivation distribution) modelled by M(t), and extended with a fatigue term F(t) that will limit the available effort when the person is fatigued.

The function $E_{HA+L}(t)=E_{HA+L}(t)$=FUEL(HA(SPL(t), SNR (t), P(t)), F(t), M(t)) extends the dynamic FUEL model by taking hearing aid processing into consideration, by simulating the dynamic processing of the hearing aid on the SPL and SNR. The hearing aid enhancement is generalized to multiple hearing aid models and brands by modelling the input difficulty as function of SPL and SNT modify it by changing the sound pressure level (SPL) and signal to noise ratio (SNR) as function of those two inputs and current program/settings P(t). This can be performed by applying the setting distribution as discussed in FIG. 1. An advantageous part of the modelling is that the result of the hearing aid enhancement is not restricted to be positive and helpful. The method by Hagerman & Olofson 2004 defines a difference in the SNR at the input side and the output side, which depending on settings, SPL, and SNR leads to enhancement (when positive) and disbenefits (when negative, due to artefacts) (Hagerman, B., & Olofsson, A. (2004). "A method to measure the effect of noise reduction algorithms using simultaneous speech and noise." Acta Acustica United with Acustica, 90(2), 356-361, hereby incorporated by reference in its entirety).

As a simple example, imagine a noisy situation where HA(SPL(t),SNR(t),P(t)) could enhance the SNR(t) by 6 dB and thus make reduce the effort as if the SNR had been 6 dB better than the current situation leading to reduced effort in that instance. The model is not limited to the enhancements, as it can also model artefacts, and thus imagine another simple situation where SNR is already high, HA(SPL(t), SNR(t), $P_{max}$(t)) would lower the SNR whereas HA(SPL(t), SNR(t), $P_{moderate}$(t)) would maintain it. Consequently, when all other parameters remain the same, the $P_{max}$ program would lead to higher effort than the $P_{moderate}$ program for that situation.

Figure 3:
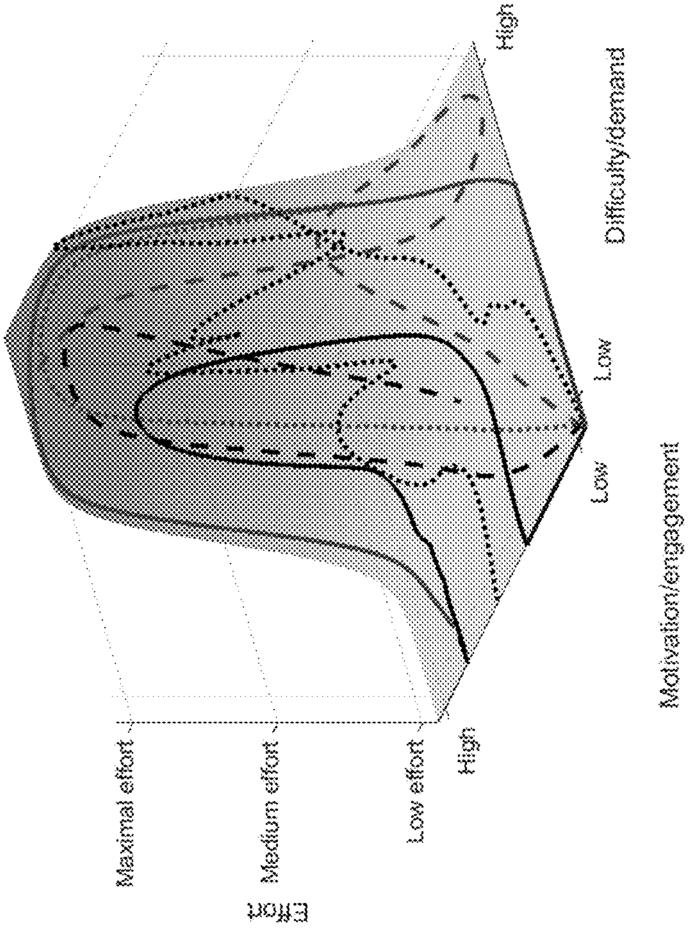
FIG. 3 shows an example model comparing effort, difficulty, and motivation for a particular user in a number of time periods according to the disclosure.

FIG. 3 shows an example model comparing effort, difficulty, and motivation for a particular user in a number of time periods according to the disclosure.

This model of FIG. 3 shows different time periods which a person can experience with different duration in effortful and less effortful situations. FIG. 3 in particular shows examples of days sampled from an individual user. For simplicity, all days start at low demand and engagement. The difficulty/demand can be estimated from hearing aid logging data (e.g., environmental data) describing the sound pressure level, the signal to noise ratio, and/or the noise floor. The effort can be estimated from pulse data (e.g., physiological data) collected in synchrony with the hearing aid logging data after accounting for the impact of physical movement on the pulse data.

When a user has worn the hearing aid for a few weeks, a statistical distribution (e.g., the effort distribution and the environmental difficulty distribution) as function of time can be established, and with the pulse data (or equivalent subjective ratings) the statistical distribution for effort and motivation as well as the integration of effort into fatigue can be established. Data synthesis can be used to generate the plurality of estimated future time periods that this user could experience.

Now, consider a single path (e.g., a time period). The simulation will consider days generated by the data synthesizer (and actual days) (e.g., the environmental difficulty distribution and the effort distribution) and simulate if adapting the settings (e.g., the setting distribution) throughout the day can lower the effort and thereby reduce the fatigue. The simulation is fed with details about the hearing aid processing so that it knows in which situations the hearing aid can provide more help (attenuation noise) more and in which situations where that is not possible. In some situations a user can have selected a different setting and the impact of that setting can be assessed from the subjective and objective collection of effort and fatigue to determine the updated setting distribution.

Figure 4:
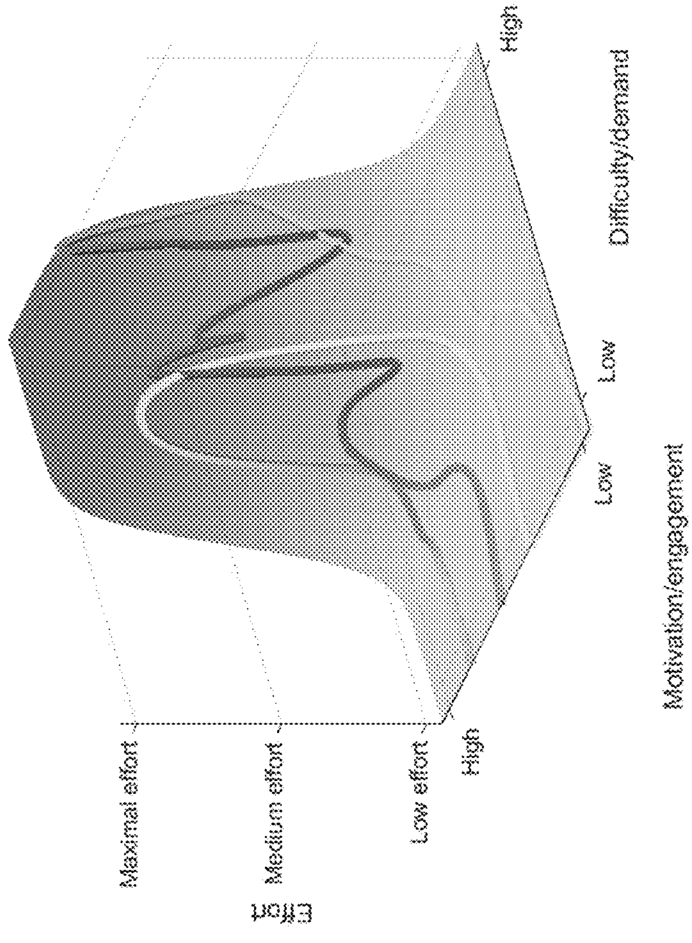
FIG. 4 shows an example model comparing effort, difficulty, and motivation for a particular user in a plurality of estimated future time periods according to the disclosure.

FIG. 4 shows an example chart comparing effort, difficulty, and motivation for a particular user in a plurality of estimated future time periods according to the disclosure. FIG. 4 illustrates a first round of the plurality of estimated future time periods (for example simulations. In certain examples, when the plurality of estimated future time periods has been completed, then an adaptive processing can be transferred to the hearing aid, such that the hearing aid adjusts the level of noise reduction in response to the baseline setting (e.g., based on the updated setting distribution), and the individual needs based on the accumulated and expected effort and fatigue. As shown in FIG. 4, the darker curve on the surface, the more fatigued the person is.

As mentioned, embodiments of the method disclosed herein can be used iteratively, and thus further future time periods can be generated (for example as a second round of simulations). In a second round of simulations (e.g., the second estimated plurality of time periods), after the hearing aid has been in use with the updated setting distribution, and usage data has been collected (environmental difficulty distribution, effort distribution, hearing aid data, hearing aid operation, pulse, subjective mood/fatigue) the method is updated with simulating hearing days.

Figure 5:
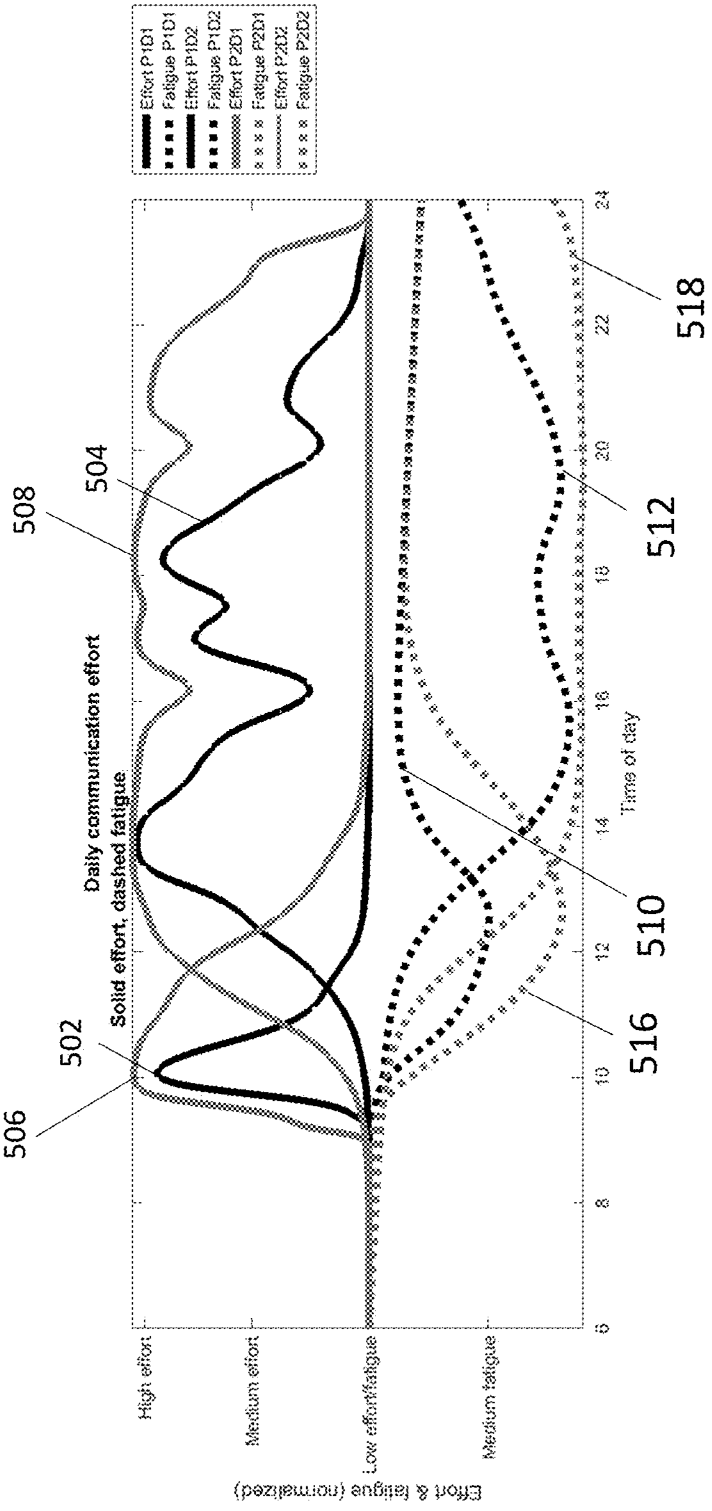
FIG. 5 shows an example model of effort and fatigue for a user according to the disclosure.

FIG. 5 shows an example chart of effort and fatigue for a user according to the disclosure. As shown in FIG. 5, there are hearing time periods D1 and D2. P1 and P2 represent two different updated setting distributions over the two time periods D1 and D2.

As shown in FIG. 5, line 502 is the effort distribution for P1D1 and line 504 is the effort distribution P1D2. Line 506 is the effort distribution for P2D1 and line 508 is the effort distribution for P2D2. Line 510 is the fatigue experienced by the user for P1D1, line 512 is the fatigue experienced by the user for P1D2, line 514 is the fatigue experienced by the user at P2D1 and line 516 is the fatigue experienced by the user at P2D2. Accordingly, as shown the setting distribution P1 is better suited to the user as both effort and fatigue are optimized.

Figure 6:
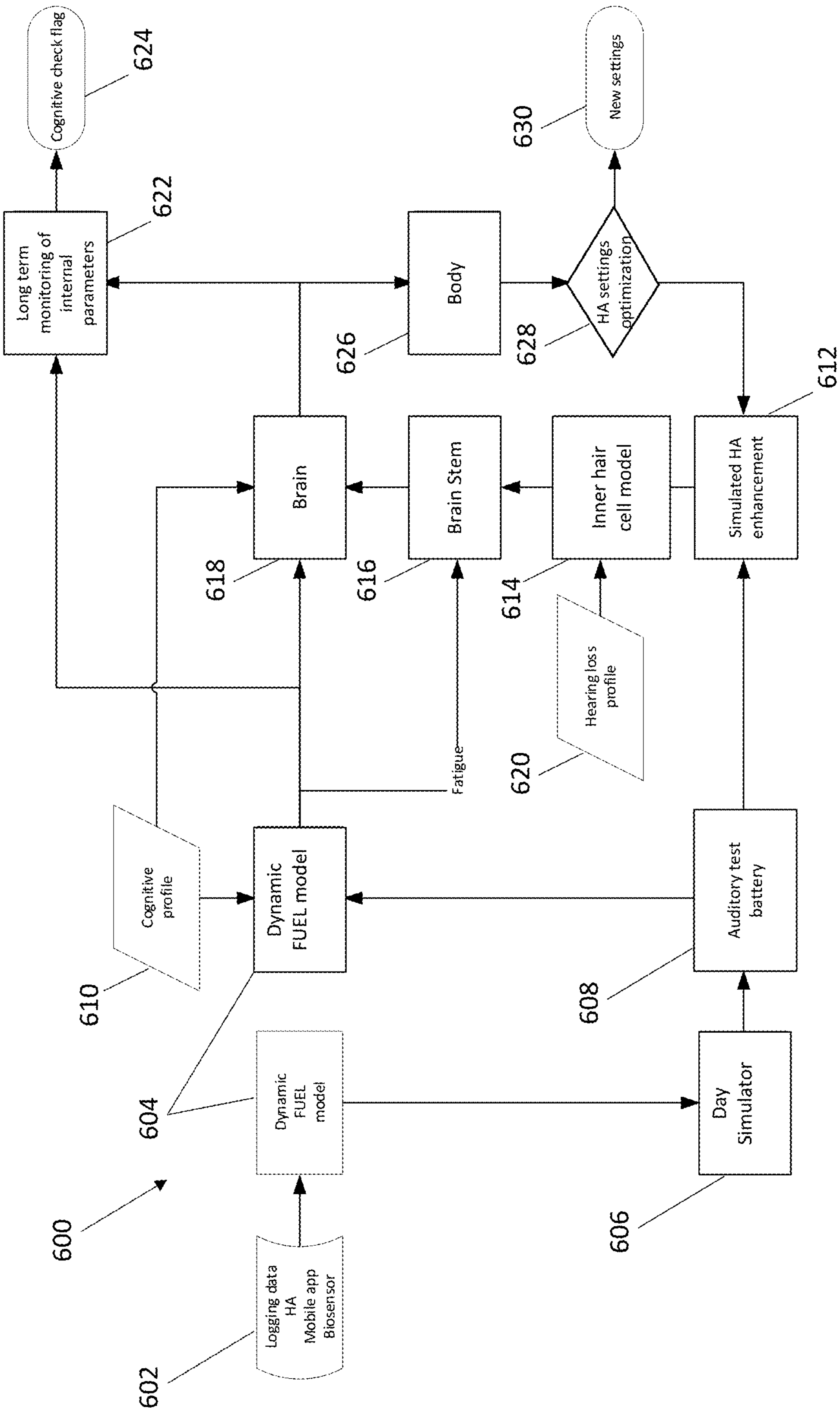
FIG. 6 shows an example implementation of the method according to the disclosure.

FIG. 6 shows an example implementation 600 of the method according to the disclosure. As shown, the implementation 600 can obtain logging data 602 (for example environmental data and/or physiological data). This can be performed by a hearing aid (HA), mobile app (e.g., via user input) and/or a biosensor. This logging data can then be entered into the dynamic FUEL model 604 as discussed herein. The dynamic FUEL model 604 can apply the method steps as discussed herein. The dynamic FUEL model 604 may be a machine learning model.

For example, the starting point for the digital twin optimization (e.g., the generating the plurality of estimated future time periods of FIG. 1) is a set of simulated days that specifies a sequence of events with varying difficulty, behavior, effort, fatigue, and program settings representative of the hearing aid user. These days are generated by applying Data Synthesizer (Ping et al 2017) to the user's data (for example environmental data and/or physiological data) logged from the hearing aid.

Once the logging data 602 is input into the dynamic FUEL model 604, the implementation 600 can generate the plurality of estimated future time periods as the day simulator 606. The setting distribution can be applied as an auditory test battery 608. The results of the auditory test battery 608 can be input into the dynamic FUEL model 604. Further, any cognitive profile 610 of the user can be input into the dynamic FUEL model 604.

An event is generated (for example, simulated) by choosing a test from a test battery of known already available listening tests, e.g., tone in noise, digit in noise, speech in noise, etc. This produces an example stimulus with a target and background, which is mixed according to the levels defined by the event and the current hearing aid setting distribution. This signal is fed through the aforementioned to the inner hair cell model 614, adopting the user's hearing characteristics through hearing loss profile 620 (thresholds, frequency resolution, temporal resolution, e.g. as described by Carney et al 2015 (Carney, L H, Li, T., McDonough, J M (2015), Speech Coding in the Brain: Representation of Formants by Midbrain Neurons Tuned to Sound Fluctuations. eNeuro 2(4) e0004-15.2015 1-1. (DOI: 10.1523/ENEURO.0004-15.2015), Mao et al 2013 (Mao, J., Vosoughi, A., and Carney, L. H. (2013), Predictions of diotic tone-in-noise detection based on a nonlinear optimal combination of energy, envelope, and fine-structure cues. (JASA 134:396-406)), Zilany et al 2009 (Zilany, M. S. A., Bruce, I. C., Nelson, P. C., and Carney, L. H. (2009), A phenomenological model of the synapse between the inner hair cell and auditory nerve: Long-term adaptation with power-law dynamics. (JASA 126:2390-2412)), the three articles of which are hereby incorporated by reference in their entirety). The output is fed through a transmission line (the brain stem model 616) that enhances or deteriorates the signal quality based on effort and motivation (modeled as an adaptive internal noise parameter). This is fed to the brain model 618 that estimates the effort associated with the event. The effort is then fed to the body 626, modelled by the fatigue function F(t).

In other words, the auditory test battery 608 can also be input into a simulated hearing aid enhancement 612. The simulated hearing aid enhancement 612 can be used to determine cognitive and/or fatigue results, such as by way of an inner hair cell model 614, for example using brain model 618, and brain stem model 616. Further, a user's hearing loss profile 620 can be incorporated into the inner hair cell model 614. The dynamic FUEL model 604 can also be incorporated into the brain stem model 616 and brain model 618. For example, parameters indicative of fatigue can be output from the dynamic FUEL model 604. Moreover, the cognitive profile 610 can be incorporated into the brain model 618.

The output of the dynamic FUEL model 604 and the brain model 618 can be used for long term monitoring 622 of internal parameters of a user and/or hearing aid, which can also be used to check for cognitive parameters 624.

Further, the brain model 618 can be used to as input for body model 626, which in turn can be used for hearing aid setting optimization 628, such as for determining an optimized effort distribution. Based on the optimization 628, an updated setting distribution (e.g., new settings) 630 can be determined. Further, the optimization 628 can be incorporated back into the simulated hearing aid enhancement 612 for further development.

Introducing the optimization in the digital twin (e.g., via determination of an optimized effort distribution), the above process is repeated for the sequence simulating a day and adapting the P(t) function over a cost function penalizing excessive fatigue and excessive effort.

The optimized PO(t) is an adaptive program that increases the enhancement when the current event would lead to either excessive fatigue and or excessive effort.

For applying the output of the digital twin optimization, the adaptive optimized PO(t) is transferred to either a mobile app or a hearing aid that has access to both sound data, hearing aid data, and body response data.

Once the hearing aid is in use with the adaptive optimized program PO(t), the optimization can continue, by updating data that goes into the simulated days, so that it continues to adapt to the users' situations.

However, while the adaptation to the user's situations is beneficial for the hearing aid processing, long term monitoring 622 for changes in the internal parameters describing the user in the aforementioned models can indicate changes to cognitive capabilities. For example, if a person suddenly begins to exhibit more effort compared to similar situations in the past, and that updating the hearing settings does not improve on this, then the digital twin can alert 624 the person to have a cognitive assessment. Likewise, if the person maintains the effort level, but decreases the difficulty of situations this also leads to such an alert 624. The common denominator for both alerts 624 is that the long-term monitoring 622 of the internal parameters will reveal that daily communication tasks require more effort, which could lead to exhibiting more effort or avoiding the effort.

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element, but an intervening element may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method are not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein but are to be accorded the full scope consistent with the language of the claims, wherein reference to an element in the singular is not intended to mean "one and only one" unless specifically so stated, but rather "one or more." Unless specifically stated otherwise, the term "some" refers to one or more.

The invention claimed is:

1. A method of cognitive adaptation for a hearing aid to a user, the method comprising:

determining, based on environmental data obtained by the hearing aid over a time period, an environmental difficulty distribution over said time period;

determining, based on physiological data of the user over the time period, an effort distribution over said time period;

determining, based on the environmental difficulty distribution and the effort distribution, a setting distribution of the hearing aid indicative of a hearing setting of the hearing aid over said time period configured to optimize the effort distribution;

generating, based on the environmental difficulty distribution and the effort distribution, a plurality of estimated future time periods, each of the plurality of estimated future time periods comprising an estimated environmental difficulty distribution and an estimated effort distribution;

applying the setting distribution to each of the plurality of future time periods for determination of an optimized effort distribution;

determining, based on the optimized effort distribution, an updated setting distribution; and applying the updated setting distribution to the hearing aid.

2. The method of claim 1, wherein determining the setting distribution comprises:

obtaining user input during the time period; and determining, based on the user input, the environmental difficulty distribution and the effort distribution, the setting distribution.

3. The method of claim 1, wherein the estimated environmental difficulty distribution and/or the estimated effort distribution vary between each of the plurality of future time periods.

4. The method of claim 1, further comprising determining, based on the environmental difficulty distribution, the effort distribution, and user motivation input, a motivation distribution over said time period.

5. The method of claim 4, wherein generating the plurality of estimated future time periods is based on the motivation distribution, the environmental difficulty distribution, and the effort distribution, the plurality of estimated future time periods, each of the plurality of estimated future time periods comprising an estimated motivation distribution, the estimated environmental difficulty distribution, the estimated effort distribution.

6. The method of claim 4, further comprising determining a cognitive capability parameter indicative of a dynamic cognitive capability of the user based on the motivation distribution, the environmental difficulty distribution, and the effort distribution.

7. The method of claim 6, wherein determining the updated setting distribution is based on the optimized effort distribution and the cognitive capability parameter.

8. The method of claim 1, wherein the environmental data comprises one or more of: sound pressure level, signal to noise ratio, and noise floor.

9. The method of claim 1, further comprising:

generating, based on the estimated environmental difficulty distribution and the estimated effort distribution, a second plurality of estimated future time periods, each of the second plurality of estimated future time periods comprising a second estimated environmental difficulty distribution and a second estimated effort distribution;

applying the updated setting distribution to each of the second plurality of future time periods for determination of a second optimized effort distribution;

determining, based on the second optimized effort distribution, a second updated setting distribution; and applying the second updated setting distribution to the hearing aid.

10. The method of claim 1, wherein the time period is a week or greater.

11. The method of claim 1, wherein the physiological data is pulse data.

12. The method of claim 11, further comprising obtaining the pulse data from an external device.

13. The method of claim 1, wherein the environmental data and the physiological data are past data.

14. The method of claim 1, wherein the environmental data and the physiological data are live data.

15. The method of claim 1, further comprising providing the environmental difficulty distribution and the effort distribution to a machine learning model and wherein the setting distribution is output by the machine learning model.

* * * * *